United States Patent
Josic et al.

(10) Patent No.: US 6,319,401 B1
(45) Date of Patent: *Nov. 20, 2001

(54) DEVICE FOR THE RAPID SEPARATION AND/OR CONVERSION OF SUBSTRATES

(75) Inventors: Djuro Josic, Vienna (AT); Primoz Koselj, Ljubljana (SI); Ales Podgronik, Izola (SI); Ales Strancar, Ajdovscina (SI)

(73) Assignee: BIA Separations d.o.o., Ljubljana (SI)

( * ) Notice: Subject to any disclaimer, the term of this patent is extended or adjusted under 35 U.S.C. 154(b) by 0 days.

This patent is subject to a terminal disclaimer.

(21) Appl. No.: 09/276,711

(22) Filed: Mar. 26, 1999

Related U.S. Application Data

(63) Continuation of application No. 08/518,511, filed on Aug. 23, 1995, now Pat. No. 5,972,218.

(30) Foreign Application Priority Data

Aug. 23, 1994 (DE) .............................................. 94 113 105

(51) Int. Cl.[7] .................................................. B01D 65/00
(52) U.S. Cl. .................... 210/321.78; 210/445; 210/446; 210/455; 210/456; 210/488; 210/490; 210/500.34; 210/500.35; 210/506
(58) Field of Search ................................. 210/321.78, 445, 210/446, 455, 456, 488, 490, 500.34, 500.35, 506, 450, 453

(56) References Cited

U.S. PATENT DOCUMENTS 3,483,990 * 12/1969 Litle et al. .......................... 210/321.2
5,972,218 * 10/1999 Josic et al. ....................... 210/321.78

* cited by examiner

*Primary Examiner*—Matthew O. Savage
(74) *Attorney, Agent, or Firm*—Jacobson Holman, PLLC

(57) ABSTRACT

A device for the rapid separation and/or conversion of substrates is disclosed herein. The device include a porous tube (2) disposed inside a tubular sample distributor (3). The tubular sample distributor (3) includes channel structures on its inner surface and is disposed inside a tubular body (4). A tubular sample collector (1) having channel structures on its outer surface is disposed inside the porous tube (2). A circular sample distributor (7) is provided having a circumferential portion and radially extending grooves in conjunction with the channel structures of the tubular sample distributor (3). A circular sample collector (8) is also provided having a circumferential portion and radially extending grooves in conjunction with the channel structures of the tubular sample collector (1). The hollow body (4) is arranged between securing means (5) that provide a sample inlet and outlet in communication with the circular sample distributor (7) and circular sample collector (8), respectively.

9 Claims, 4 Drawing Sheets

DEVICE FOR THE RAPID SEPARATION AND/OR CONVERSION OF SUBSTRATES

Figure 1:
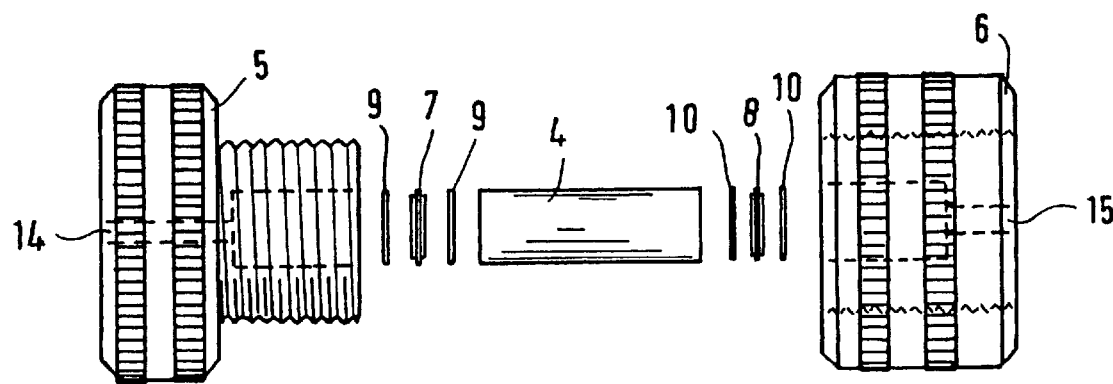

This application is a continuation of U.S. patent application Ser. No. 08/518,511, filed on Aug. 23, 1995, now U.S. Pat. 5,972,218.

The invention is concerned with a process for the conversion of substrates both for analytical and preparative purposes in a flow-through and a cross flow reactor, a separation and/or conversion device, an analytical device as well as filtration device for carrying out such processes.

The use of membranes for separation of biopolymers in analytical scale has been proven to be very efficient. Also the separation of biopolymers with membrane-immobilized affinity molecules is possible. Josic et al. disclose in "Journal of chromatography", 590, (1992), pages 59–76, porous discs made of poly(glycidylmethacrylate) which can be used for high-performance membrane chromatography (HPMC) of proteins. Separations of standard proteins by anionexchange HPMC using a DEAE disc were carried out. It is reported that separations on HPMC discs could be carried out faster than corresponding separations on HPLC columns. The pressure drop on the discs was low even at high flow-rates. There were separated standard proteins and serum membrane proteins on compact discs modified with heparin and collagen as ligands.

Abou-Rebyeh in "Journal of Chromatography", 566, (1991), pages 341 to 350, disclose that membrane supports as stationary phase, coupled with ligands can be used for affinity membrane chromatography for purification of the enzyme carbonic anhydrase from hemolysate of human erythro-cytes.

WO 89/09280 discloses a process for detecting compounds which can take up or give off electrons when catalysed by oxidases. To continuously detect compounds a sample solution is continuously taken from a fermentation solution, then conducted over a filter and thereafter through a carrier substance, on which oxidases and possibly other enzymes are immobilized and which is contained in a mini-column. Then the peroxide formed the solution leaving the column is quanitatively analysed by electrochemical detection.

FR-A-2,283,903 discloses enzymatic columns containing membranes having biological activity as well as application of such columns in analytical methods.

FR-A-2,405,744 discloses a radial reactor for carrying out reactions which are catalysed by enzymes.

EP-A-0 019 638 discloses an immobilized enzyme column which can be used in a chemical autoanalyzer for analyzing materials contained therein such as blood serum or urine. An enzyme is utilized in clinical test and comprises one, two or more columns.

U.S. Pat. No. 5,310,526 disclosed a chemical sensor and method for in-line chemical analysis including a body having a central cavity. The body also has a pair of openings through it to the cavity a porous plug, such as a ceramic frit, is sealed into each of this openings so that there is a space between the plugs in the cavity. A component of interest of the sample reacts with a reactive component of a reagent in the cavity to produce the reaction product which is monitored.

Chemical and Engineering News, Vol. 58, No. 30, Pennsylvania, USA discloses that membranes may simplify catalytic reactions. The prototype system described there has two membranes sandwiched together. The first membrane is a Goretex membrane filled with a decyl alcohol solvent and the second membrane is made of porous cellulose and has an enzyme bound to it.

U.S. Pat. No. 3,308,558 discloses an environmental chamber unit for the study of aerosols.

Besides modified membranes also modified porous discs are useful in purification techniques.

However, the methods described can either not be used for preparative scale separations or conversions but only with modifications which render the process unreproducible and very uncomfortable to be used. The separation units in the device available at present do not withstand, for example, the conditions which must be applied if the membrane or porous disc are working in a preparative and industrial scale or in the mode of fast analysis. The membranes or discs tend to be destroyed under the influence of the high pressure which must be applied under preparative conditions. Moreover, the sensitivity of the separation units towards mechanical stress requires the application of the sample to be treated in a large volume. That in turn leads to loss of separation power of the methods since "peak" broadening of the eluting substances occurs and the separation time is prolonged. With regard to the conversion of products in a preparative scale using that kind of chromatography nothing is known up to now. Here, it is also essential to have so small a volume as possible to apply in order to keep the eluting fractions with substances so small as possible or the concentration of the eluted substances so high as possible.

The conventional processes and equipments cannot warrant simultaneously (i) a fast preparative and analytical process;

(ii) a sufficient reproduceability of the result of the separation or conversion;

(iii) a feasible duration and lifetime of the equipment used;

(iv) purification and/or conversion of substrates from a suspension containing high amounts of solid particles.

Other conventional methods for separation and conversion of substances are working in the time range of minutes. This, however, is too slow for utilizing such methods in on- and in-line control of chemical or biotechnological methods and for in-process purification an/or conversion of the respective products.

One object of the invention is to provide a reliable and fast method for separation and conversion of substrates. The method should be applicable in a preparative and analytical scale.

Another object of the invention is to avoid a purification or conversion of substrates leading to diluted fractions of material. Yet another object is to provide devices for carrying out the processes of the invention as well as processes known in the art.

The objects addressed above are solved by a process having the features of claim 1. Subclaims 2 to 11 are preferred embodiments of the process of the invention. A separation and/or conversion device which is useful for carrying out the process of the invention comprises the features of claim 12. Subclaims 13 to 18 are preferred embodiments of the separation and/or conversion device, claim 19 concerns a cross-flow device whereas the analytical device of the invention shows the features of claim 20 and the filtration and/or separation device comprises the features of claim 21. Preferred embodiments of the filtration and/or separation device comprises the features as shown in subclaims 22 to 25 and claim 26 concerns two alternative modes of operation.

Figure 2:
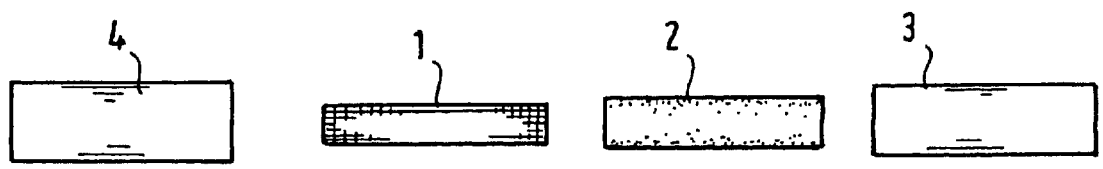
Figure 3:
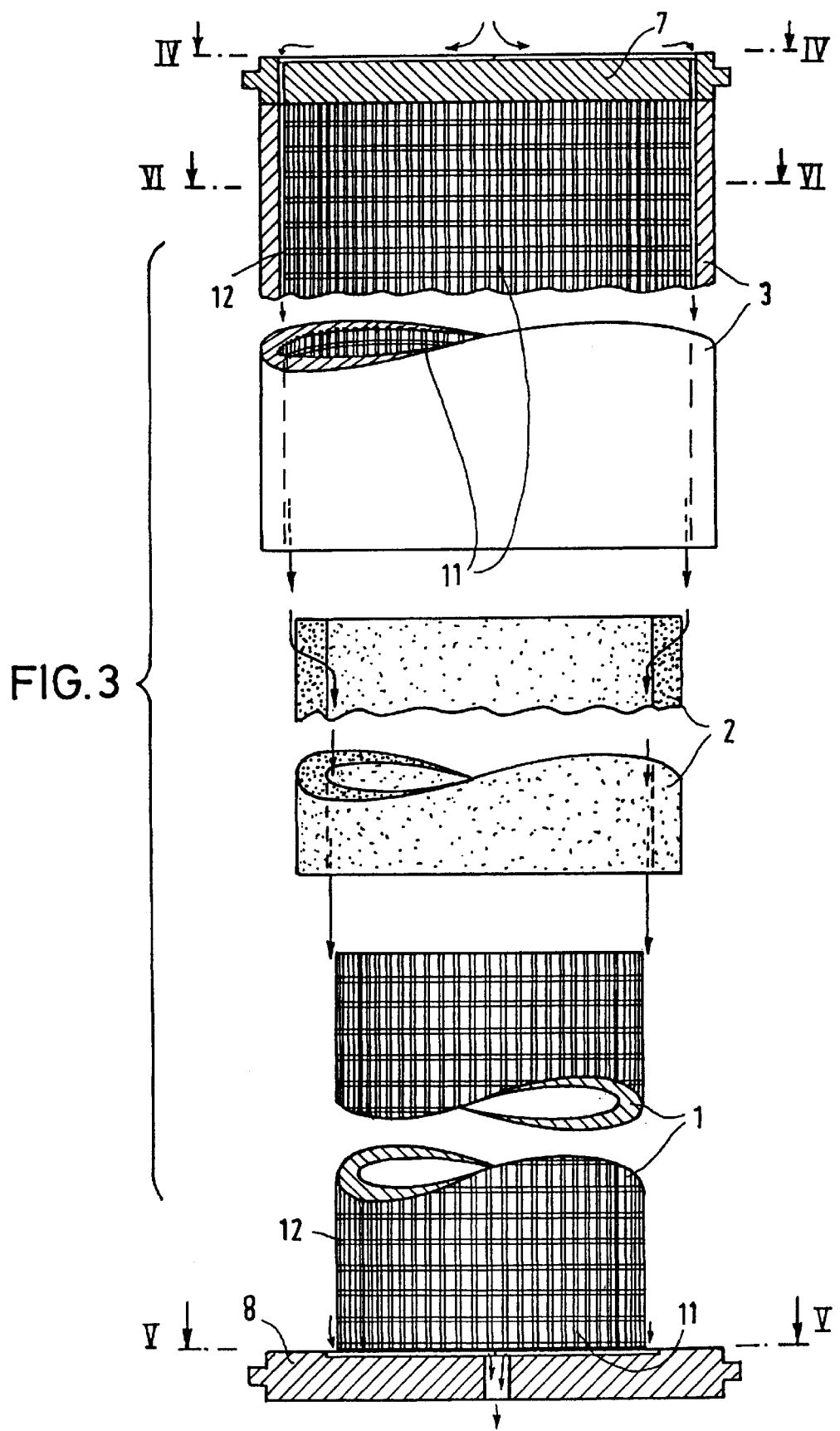
Figure 4:
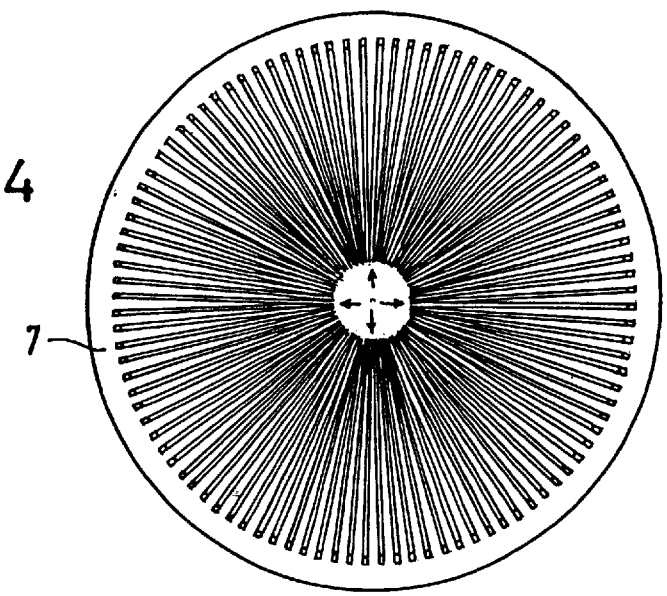
Figure 6:
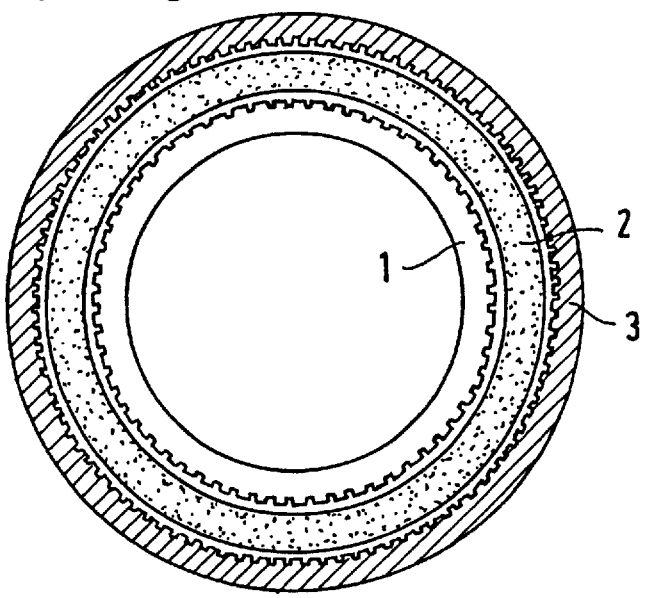
Figure 5:
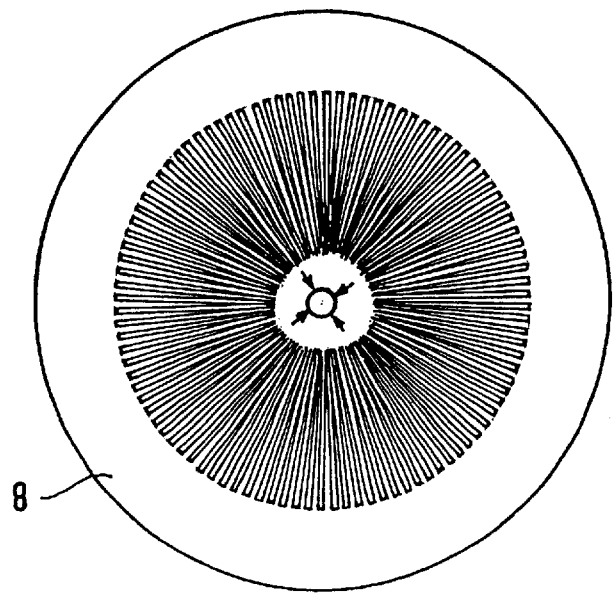
Figure 7:
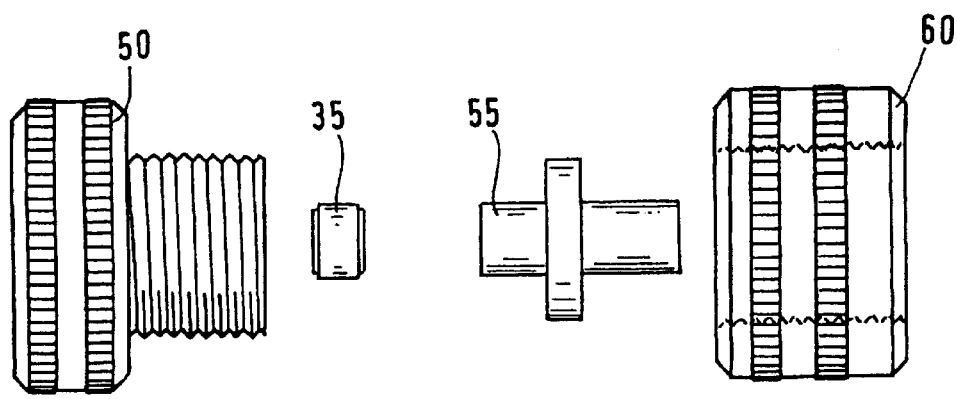
Figure 8:
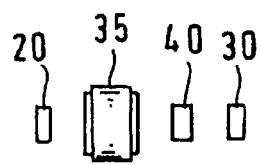

| | |
|---|---|
| FIG. 1 | shows a separation and/or conversion device of the invention in an unscrewed and disassembled arrangement of its parts. |
| FIG. 2 | shows the arrangement of the disassembled hollow body 4. |
| FIG. 3 | shows various views of the arrangement of porous tube 2, sample distributor 3, and sample collector 1. |
| FIGS. 4, 5 and 6 | show cross-sectional views of the arrangement of FIG. 3. |
| FIG. 7 | shows the analytical device of the invention in unscrewed view. FIG. 8 shows details of the holding means 35 of FIG. 7. |
| FIG. 9 | shows a filtration and/or separation device of the invention. |

The process according to the invention can be used for the conversion of substrates both for analytical and preparative purposes in a flow-through and cross-flow reactor having compact porous discs and/or tubes as carrier for conversion reactions. The membranes and/or compact porous discs and/or tubes are modified with substances being capable of specifically binding and/or converting said substrates by distributing the samples to be converted and/or preparatively separated and collecting the converted or separated substrates in a low volume, wherein the distribution of the sample does not affect the carrier adversely. The modifying substances may also be ligands which are able to minimize or prevent non-specific interactions. Non-specific interaction may cause detrimental effects such as irreversible binding and/or denaturation of the substrates to the carrier-material of the compact porous disc and/or tube. The use of such modifying substances is also advantageous since the capacity of the separation and/or conversion units may be enlarged. Preferably, the substances having hydrophilic properties are employed.

Preferably, the substances being capable of specifically binding and/or converting substrates and/or ligates are cells, organelles, high or low molecular weight substances, e. g. enzymes or other substances which can bind specifically the substrates and/or ligates with high affinity. The modifying substances having hydrophilic properties are preferably anion-exchange-materials such as disclosed in EP 0 337 144 A1 which are known under the term "tentacle exchanger".

The substances which are capable for converting or binding the ligates and/or substrates are preferably immobilized on the inner and/or outer surface of the compact porous discs and/or tubes. The inner surface of the compact porous disc and/or tube can be also understood to be part of the outer surface, e.g. if the surface of a pore is meant.

The compact porous disc and/or tube which can be used in the process of the invention preferably comprises fibers of cellulose or polymers which are modified on the surface or in the porous disc or the wall of the compact porous tube with the substances being capable of specifically binding and/or converting substrates on non woven fabrics manufactured from these fibers. The compact porous discs and/or tubes are preferably discs and/or tubes manufactured from natural polymers such as cellulose, artificial polymers such as glycidylmethacrylate polymers as well as formed copolymers such as those of polystyrene and divinylbenzene being modified with substances which are capable of specifically binding and/or converting substrates and/or ligates on their surface or inner and outer surface (channels or pores).

The areas of the inner or outer surface of the compact porous discs and/or tubes which are at least partially modified with immobilized ligands are to be understood as active surfaces.

Typically, the substrates to be converted according to the invention are e.g. naturally occurring compounds e.g. antibiotics, saccharides or peptides as well as high molecular substrates such as biopolymers e.g. proteins, nucleic acids, polysaccharides, pectines or physiologically active substrate such as enzyme inhibitors or whole cells or parts thereof.

These substrates can be easily converted at the active surface of the modified compact porous discs and/or tubes according to the invention.

The process according to the invention can be employed in the chemical, pharmaceutical, food industries or environmental technology. However, as the skilled person understands, the gist of the process is not limited to these applications. The process of the invention is especially valuable because it can be used in an in-process analytical or preparative procedure.

Another preferred embodiment of the process of the invention is its application as a very fast analytical method. The process of the invention can be used for the detection of substances in mixtures thereof in manufacturing processes by separating the substances to be detected from a reaction mixture.

Two alternatives are preferred. The first one is that a part of the reaction mixture is separated from the reactor and the substance to be detected is separated by means of compact porous discs and/or tubes as described above and detected by means of a detection system. Secondly, the substance to be detected can be separated by means of compact porous discs and/or tubes as described above, which are arranged in the reaction mixture placed in the reactor, and the substance is detected by means of a detection system.

In this embodiment the substance to be detected can also be generated from a precursor molecule or can be modified by substances which are immobilized on compact discs and/or tubes and which substances are capable of specifically binding and/or converting substrates and/or ligates.

Preferably the immobilized substances (ligands) are enzymes, affinity ligands such as antibodies, lectines or other biopolymers having properties of a receptor. Also in this embodiment the compact porous discs and/or tubes are preferably manufactured from copolymers of polystyrene and divinylbenzene or glycidylmethacrylate polymers as well as some modified natural polymers such as modified cellulose.

The process of the invention renders possible both the analytical and preparative separation of substrates as well as a conversion of substrates. Basically the mixture to be separated or the compound to be converted in a crude mixture or in more or less pure form are applied onto a compact porous disc and/or tube in a mobile phase. The mobile phase is preferably a homogenous solution of the respective mixtures.

The process of the invention is advantageous since it provides a rapid method for preparative separation of substrates and a large scale converting process of substrates. The respective fractions can be isolated in relative small volumes. Therefore, the reliability of the separation method becomes excellent. The support of the compact porous disc or tube renders possible the application of high flow-rates without causing a damage of the separation units such as the compact porous disc and/or tube.

The process of the invention can also be worked out in the simulated moving bed (SMB) as well as the continous moving bed (CMB) techniques both for separation as well as conversion operations. These techniques are well known to the person of ordinary skill in the art.

In principle, a separation and/or conversion device of the invention may be employed as a flow-through reactor as well as a cross-flow reactor. Both modes of operation require a device comprising a hollow body comprising a sample distributor, and a compact porous tube for conversion and/or separations of substrates.

In the flow-through mode of operation a liquid flow carrying the sample to be treated passes the device of the invention in a longitudinal direction. This mode is operatable for most of the separation and/or conversion problems. In the cross-flow mode of operation a liquid flow carrying the sample to be treated is introduced into the device of the invention perpendicular to the direction in which the liquid will pass through the device. The latter kind of operation is particularly useful when a liquid flow having particles or colloid solutions are to be processed without initial filtration steps. Then the liquid contacts predominantly the surface of the compact porous tube or disc, but does not penetrate the interior parts of the compact porous tube or disc. If the surface of the compact porous tube or disc is modified the sample is predominantly interacting with the active surface. Preferably, the surface of the compact porous tube or disc is provided with structures facilitating the flow of the liquid through that device. On the surface of the porous tube e.g. may be engraved channels coiling over the entire surface of the tube.

In a preferred embodiment the separation and/or conversion device of the invention comprises a hollow body comprising a sample distributor, a sample collector and a compact porous tube. The sample collector minimizes dead volume so that e. g. high resolution of separation becomes possible.

Preferably, the sample distributor is built up by a tubular sample distributor and a circular sample distributor and a sample collector having a tubular and a circular disc like shape.

Another preferred embodiment of the device of the invention comprises a sample collector, which is formed by a hollow cylinder having channel-like structures on its outer surface and the sample distributor, which is also formed by a cylinder having channel- like structures on its inner surface. The circular sample collector or sample distributor has preferably radially extending perforations, which are in conjunction with the channel-like structures of the sample collector or the sample distributor respectively. The conjunction is particularly arranged at the circumferential portion of the circular sample collector or sample distributor.

The hollow body can be arranged between two holding means providing a sample inlet and outlet.

The number of channel-like structures engraved in the inner surface of the tubular sample distributor and of the outer surface of the tubular sample collector are depending on the diameter and length of the compact porous tube. The larger or longer the tubes the higher should be the number of channel-like structures. Typically, the channel-like structures have a width of 0.1 $\mu$m to 20 $\mu$m and are extending over the entire surfaces. The distance between the channel-like structures perpendicular to the channel-like structures in axial direction is preferably in the range of from 0.2 $\mu$m to 40 $\mu$m depending on the number of such channels.

The capacity of the separation and/or conversion device covers the range of from 0.1 gram to 10 kg. of course, since it is readily possible to scale-up the dimensions of the porous tubes also higher capacities can be reached.

The tubular porous sample collector carrying the membrane is advantageous since the porous membrane has a support on its entire surface so that it is able to withstand high flow rates. The sandwich-like arrangement of membrane between the sample distributor as outer limitation and sample collector as inner limitation provides a very low dead volume which is an essential prerequisite for carrying out preparative membrane chromatography with good results. For some applications it can be advantageous to use a simplified embodiment of the device of the invention in which the sample collector has been omitted.

The analytical device comprises a compact porous disc and/or tube, which is arranged in holding means between sample distributors, securing means, which can be screwed into one another. The securing means comprise a reception for inlet and outlet of the sample.

The filtration and/or separation device of the invention comprises a hollow body, through which a liquid can flow. The hollow body is in direction of the flow partially in contact with a compact porous disc and/or, whereby the membrane or the compact porous disc is arranged in a sealing housing, which comprises an outlet. The outlet is connectable to a huisting device. In the area of the connection between hollow body and membrane or compact porous disc and/or tube a device is arranged for generating mechanical vibrations.

Preferably the device for generating mechanical vibrations is an ultrasonic generator. The device for generating mechanical vibrations is arranged preferably vis-a-vis the area of the connection between the hollow body, which can be flowed through, and the compact porous disc and/or tube.

Preferably the hollow body is of a cylindrical shape like a chromatographic column in volume of the hollow body parallel to the basis of the cylinder. There is arranged a membrane or a compact porous disc separating the lumen in an upper and a lower area. The upper partial lumen of the upper area has a small volume. An inlet and outlet of the sample to be treated, is arranged in the lower area of the device. The outlet of the partial flow through the porous disc and/or is carried out by means of a conduit which is arranged in the upper portion of the cylinder and the device for generating mechanical vibrations is arranged so that the lower partial lumen is capable of being set in motion by that vibrations.

Preferably, the diameter of the compact porous discs is in the range of from 5 mm to 100 mm and the height ranges of from 1 mm to 500 mm. The inner diameter of the compact porous tubes ranges of from 5 mm to 2,000 mm, the length ranges of from 50 to 10,000 mm and the thickness of the wall of the porous tube ranges from 2 mm to 200 mm. These ranges are typically but not limiting. The FIGS. 1 and 2 show a preferred embodiment of the separation and/or conversion device according to the invention. The hollow body 4 comprises a sample distributor 3, a sample collector 1 and a modified compact porous disc and/or compact porous tube 2. The hollow body 4 can be secured between two securing means 5,6. Disc-like sample distributors (circular distributors) 7,8 are placed at both ends of the hollow body 4. The arrangement can be sealed by the O-rings 9,10.

FIG. 3 shows a cylindrical tube 1, on the convex surface of which channels 11 are arranged in longitudinal direction and channels 12 crossing perpendicular the longitudinal channels forming a rectangular grid of channels on the surface of the tube. The tube 1 is inserted in a porous tube 2 the surface of which is modified by the substances being capable of specifically binding and/or converting substrates. In another embodiment on the tube 1 is arranged a membrane which is modified with substances which are capable of specifically binding and/or converting substrates. The disc-like sample collector 8 seals the down-stream end of the tube 1. Of course it is possible to turn around the mode of operation by using the sample collector 8 portion of the device as inlet portion. Then the tube-like sample collector works as a sample distributor.

FIG. 3 shows also a view of the concave surface of a tube 3 partially cut along its longitudinal axis. Preferably, the inner surface of the tube 3 which is working e.g. as a sample distributor 3 is provided with channels 11 and 12 as mentioned above in order to achieve a low dead volume. It is preferred that the inner surface of the sample distributor 3 is arranged very closely to the porous tube 2 arranged on the sample collector 1. Most preferred is an arrangement in which the porous tube touches the outer surface of the sample collector 1 and the inner surface of the sample distributor 3. The arrangement of the tubular distributor 3 and collector 1 is sealed at one end with a circular sample distributor 7 (FIG. 4) and on the other end a circular sample collector 8 (FIG. 5). FIG. 4 is a cross-sectional view along the line IV—IV of FIG. 3 and FIG. 5 is a cross-sectional view along the line V—V of FIG. 3. The circular sample collector 8 and sample distributor 7 have radially extending grooves which are in conjunction with the channels of the tubular sample collector 1 or the tubular sample distributor 3 respectively. The conjunction preferably is arranged at the circumferential portion of the circular sample collector 8 or sample distributor 7. The hollow body 4 is preferably arranged between two holding means 5,6 providing a sample inlet 14 and outlet 15 (FIG. 1).

FIG. 6 shows a cross-sectional view through the device of FIG. 3 along the line between VI—VI. The porous tube 2 is arranged between the tube-like sample collector 1 and tube-like sample distributor 3. The space between the tubes 1,2 and 3 is not real but has been introduced for the sake of clearity of the figure.

FIGS. 7 and 8 show the analytical device of the invention. This device comprises a compact porous discs 40 which is arranged or in situ polymerized in holding means 35 between two sample distributors 20,30, two securing means 50,60 which can be screwed into one another, which securing means 50,60 comprise a reception for inlet and outlet of the sample. In order to adjust the fit of the holding means 35 between the securing means a body 55 can be arranged between the securing means 50,60.

Figure 9:
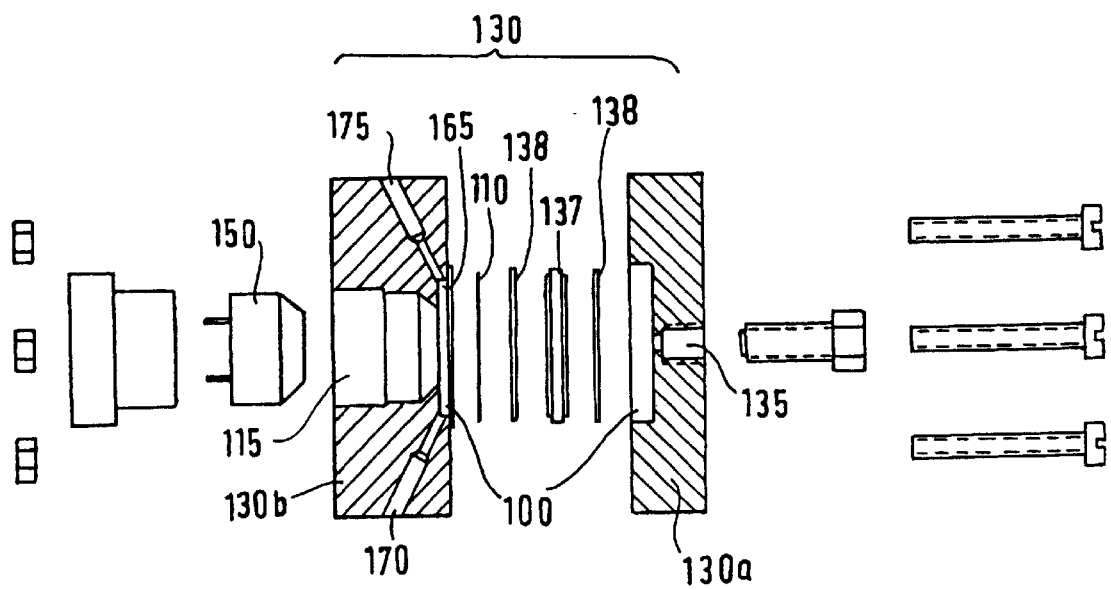

FIG. 9 shows the filtration and/or separation device of the invention. This device comprises a hollow body 100 through which a liquid can flow which hollow body 100 is in direction of the flow partially in contact with a compact disc 110. The compact porous disc 110 is arranged in a sealing housing 130 which comprises an outlet 135 which is connectable to a pumping device, the compact porous disc 110 is arranged between two O-rings 138 and a sample dispenser 137. In the area 115 of the connection Preferably the device for generating mechanical vibrations 150 is an ultrasonic generator or an electromagnetic (selenoid) actuator.

In a preferred embodiment of the filtration and separation device of the invention, the device for generating mechanical vibrations 150 is arranged vis-a-vis the area 115 of the connection between the hollow body 100 which can be flowed through, and the compact porous disc 110.

Typically, the hollow body 100 is a cylindrical tube in the lumen of which there is arranged a compact porous disc 110 parallel to the basis of the cylindrical tube. The arrangement of the compact porous disc 110 is separating the lumen in an upper and a lower area, wherein the upper partial lumen has a small volume, an inlet 170 and outlet 175 of the sample to be treated, is arranged in the lower area of the device and the outlet 175 of the partial flow through the compact porous disc is carried out by means of a conduit which is arranged in the upper portion of the cylinder and the device for generating mechanical vibrations is so arranged that the lower partial lumen 165 is capable of being set in motion by vibrations.

In particular, the process of the invention and the respective devices can be used in biotechnological processes. In a conventional bioreactor for example an antibiotic precursor molecule is produced by cultivated cells. Continuously or discontinuously a stream is taking away from the bioreactor by means of a conduit. This conduit or passes a filtration and separation device of the present invention described herein before. The fraction of interest is removed from the filtration device by a conduit and the remaining evaluate is fed back into the bioreactor through another conduit discarded. The sterility of the entire process should be provided. In the latter case the bioreactor must be fed with additional volume of the fluid in order to balance the loss of liquid. The fraction containing the antibiotic precursor molecule is then fed into a preparative column or disc tube which is described in a greater detail in FIG. 1. This device contains for example an enzyme which is converting the antibiotic precursor molecule into the active agent. Of course several conversion steps of the same or different kind can be carried out by running the sample through several devices as described in FIG. 1. After the conversion has taken place, the antibiotic containing fraction is collected and optionally further processed. Optionally, the other fractions can be fed back into the bioreactor.

Such an in-process analysis becomes possible since the separation unit of the invention allows fast separations which are at least 10 times faster than conventional HPLC-columns. An additional advantage is that the pressure drop is in average ten times lower.

The amount of product can be monitored with the analytical device. Depending on the amounts of antibiotic substance detected the manufacturing process can be optimized for example for maximum accumulation of the antibiotic or antibiotic precursor molecule.

U.S. Pat. No. 4,689,302 discloses a flow reactor for reacting a feedstock with a proteinaceous preparation immobilized on and within the pores of a support medium while traversing a spiral path between adjacent turns of that spiral. The support medium, which is disclosed, has a spacing means placed on one surface thereof. The support medium and spacing means are wound upon a porous core to form a jelly roll-like spiral configuration. The marginal edges of the reactors are sealed but provision is made to introduce or remove materials from the core and the free end of the spiral is left open to also introduce or remove materials. In a first form the feedstock is introduced into the core and the reacted feedstock is removed from the spiral free end. In a second form the introduction and removal of the feedstock and reacted feedstock is reversed. The spacing means may be a series of ribs on the support medium or may be a net-like sheets. The support medium can be built up by a porous compact disc or a respective porous sheet as has been described for the devices of the invention herein before. Thus, both the process of the invention as well as the porous discs or tubes can be utilized in bioreactors as described in U.S. Pat. No. 4,689,302.

What is claimed is:
1. A device comprising a hollow body (4), a tubular sample distributor (3) and a porous wall, characterized in that
the porous wall is a porous tube (2) for rapid separation of substrates, the porous tube (2) is manufactured from artificial polymers or copolymers, the porous tube (2) is inside the tubular sample distributor (3) which tubular sample distributor (3) is inside a tubular hollow body (4) and the tubular sample distributor (3) is formed by a cylinder having channel structures on its inner surface.

2. The device according to claim 1, comprising additionally a sample collector.

3. The device according to claim 2, further comprising a circular sample distributor (7) in conjunction with said tubular sample distributor (3).

4. The device according to claim 2, wherein the sample collector has a tubular sample collector (1) positioned inside said porous tube (2) and a circular sample collector (8) in conjunction with said tubular sample collector (1).

5. The device according to claim 2, wherein the tubular sample collector (1) is formed by a hollow cylinder having channel structures on its outer surface.

6. The device according to claim 5, wherein the circular sample distributor has a circumferential portion and radially extending grooves which are in conjunction with the channel structures of the tubular sample distributor (3) at said circumferential portion.

7. The device according to claim 6, wherein the circular sample collector has a circumferential portion and radially extending grooves which are in conjunction with the channel structures of the sample collector (1) at said circumferential portion.

8. The device according to claim 1, wherein the hollow body (4) is arranged between two holding means (5) providing a sample inlet and outlet.

9. The device according to claim 1, wherein the porous tubes have an inner diameter ranging from 5 mm to 2,000 mm, a length ranging from 50 to 10,000 mm, and a thickness ranging from 2 to 200 mm.

* * * * *